US010575986B2

(12) United States Patent
Rubinfeld et al.

(10) Patent No.: US 10,575,986 B2
(45) Date of Patent: Mar. 3, 2020

(54) OPHTHALMIC TREATMENT SOLUTION DELIVERY DEVICES AND DELIVERY AUGMENTATION METHODS (71) Applicant: CXL Ophthalmics, LLC, Encinitas, CA (US)

(72) Inventors: Roy S. Rubinfeld, Bethesda, MD (US); Wayne Korteweg, N. Stonington, CT (US)

(73) Assignee: CXL OPHTHALMICS, LLC, Encinitas, CA (US)

( * ) Notice: Subject to any disclaimer, the term of this patent is extended or adjusted under 35 U.S.C. 154(b) by 898 days.

(21) Appl. No.: 14/275,192

(22) Filed: May 12, 2014

(65) Prior Publication Data
US 2014/0249509 A1 Sep. 4, 2014

Related U.S. Application Data (63) Continuation-in-part of application No. PCT/US2013/034187, filed on Mar. 27, 2013.

(60) Provisional application No. 61/617,339, filed on Mar. 29, 2012.

(51) Int. Cl.
A61F 9/00 (2006.01)
A61K 31/525 (2006.01)
A61K 9/00 (2006.01)

(52) U.S. Cl.
CPC .................................. A61F 9/0008 (2013.01)

(58) Field of Classification Search
None
See application file for complete search history.

(56) References Cited

U.S. PATENT DOCUMENTS 3,132,068 A 5/1964 Behrman
4,098,728 A * 7/1978 Rosenblatt ............ A61L 15/425
521/141
4,676,790 A 6/1987 Kern
4,863,627 A 9/1989 Davies et al.
(Continued)

FOREIGN PATENT DOCUMENTS

CA 2319087 A1 8/1999
CA 2418306 A1 1/2002
(Continued)

OTHER PUBLICATIONS

Extended European Search Report for European patent application No. 15793441.5 dated Jan. 2, 2017.
(Continued)

Primary Examiner — Nathan R Price
Assistant Examiner — Weng Lee
(74) Attorney, Agent, or Firm — Procopio, Cory, Hargreaves & Savitch LLP (57) ABSTRACT A first sponge device for use to manipulate and prepare the surface of the epithelium of an eye prior to application of an ophthalmic solution has a handle and a sponge head secured to the handle. The head is made of an absorbent, wicking sponge material and has a non-sharp, tissue preparation surface of predetermined shape for rubbing across the surface of the epithelium layer in order to manipulate the tissue. After the surface is prepared, a second, holding sponge is placed over the eye to act as a reservoir and to hold ophthalmic solution against the eye surface.

29 Claims, 9 Drawing Sheets

(56) References Cited

U.S. PATENT DOCUMENTS

| | | | |
|---|---|---|---|
| 5,368,590 A * | 11/1994 | Itoh | A61F 9/0017 128/853 |
| 5,433,714 A * | 7/1995 | Bloomberg | A61F 9/0017 128/898 |
| 5,639,481 A | 6/1997 | Kessler et al. | |
| 5,824,073 A * | 10/1998 | Peyman | A61F 2/063 602/74 |
| 5,849,291 A | 12/1998 | Kessler | |
| 5,954,682 A * | 9/1999 | Petrus | A61F 11/00 128/898 |
| 6,043,237 A | 3/2000 | Meadows et al. | |
| 6,053,936 A | 4/2000 | Koyama et al. | |
| 6,099,521 A | 8/2000 | Shadduck | |
| 6,161,544 A | 12/2000 | Devore et al. | |
| 6,162,210 A | 12/2000 | Shadduck | |
| 6,183,086 B1 | 2/2001 | Neubert | |
| 6,248,335 B1 | 6/2001 | Duan et al. | |
| 6,309,656 B1 | 10/2001 | Pugliese et al. | |
| 6,413,268 B1 | 7/2002 | Hartman | |
| 6,447,537 B1 | 9/2002 | Hartman | |
| 6,471,691 B1 | 10/2002 | Kobayashi et al. | |
| 6,544,165 B1 | 4/2003 | McNew | |
| 6,544,286 B1 | 4/2003 | Perez | |
| 6,783,539 B1 | 8/2004 | Timberlake et al. | |
| 6,880,558 B2 | 4/2005 | Perez | |
| 6,905,641 B2 | 6/2005 | Platt et al. | |
| 7,015,252 B2 | 3/2006 | Fujii et al. | |
| 7,044,945 B2 | 5/2006 | Sand | |
| 7,073,510 B2 | 7/2006 | Redmond et al. | |
| 7,077,839 B2 | 7/2006 | Hamblin et al. | |
| 7,097,629 B2 * | 8/2006 | Blair | B08B 1/00 15/222 |
| 7,186,417 B1 | 3/2007 | Siegel et al. | |
| 7,220,278 B2 | 5/2007 | Peyman | |
| 7,288,106 B2 | 10/2007 | Heacock et al. | |
| 7,331,350 B2 | 2/2008 | Kochevar et al. | |
| 7,479,136 B2 | 1/2009 | Dotson | |
| 7,498,156 B2 | 3/2009 | Goodrich et al. | |
| 7,727,544 B2 | 6/2010 | Schwartz et al. | |
| 7,744,590 B2 | 6/2010 | Eells et al. | |
| 7,753,943 B2 | 7/2010 | Strong | |
| 7,943,590 B2 | 5/2011 | Flugelman | |
| 8,034,373 B2 | 10/2011 | Reynolds et al. | |
| 8,092,490 B2 | 1/2012 | Redmond et al. | |
| 8,100,530 B2 | 1/2012 | Zhou et al. | |
| 8,106,038 B2 | 1/2012 | Margaron et al. | |
| 8,177,778 B2 | 5/2012 | Muller et al. | |
| 8,202,272 B2 | 6/2012 | Muller et al. | |
| 8,215,314 B2 | 7/2012 | Chan et al. | |
| 8,238,993 B2 | 8/2012 | Maynard et al. | |
| 8,282,629 B2 | 10/2012 | Mrochen et al. | |
| 8,348,935 B2 | 1/2013 | Muller et al. | |
| 8,366,689 B2 | 2/2013 | Marshall et al. | |
| 8,398,628 B2 | 3/2013 | Muller | |
| 8,409,189 B2 | 4/2013 | Muller | |
| 8,414,911 B2 | 4/2013 | Mattson et al. | |
| 8,460,278 B2 | 6/2013 | Muller | |
| 8,469,952 B2 | 6/2013 | Muller et al. | |
| 8,574,277 B2 | 11/2013 | Muller et al. | |
| 8,580,789 B2 | 11/2013 | Krueger et al. | |
| 8,652,131 B2 | 2/2014 | Muller et al. | |
| 8,712,536 B2 | 4/2014 | Muller et al. | |
| 8,870,934 B2 | 10/2014 | Muller et al. | |
| 8,882,757 B2 | 11/2014 | Muller et al. | |
| 8,992,516 B2 | 3/2015 | Muller | |
| 9,020,580 B2 | 4/2015 | Friedman et al. | |
| 9,044,308 B2 | 6/2015 | Muller et al. | |
| 9,125,856 B1 | 9/2015 | Paik et al. | |
| 9,498,114 B2 | 11/2016 | Friedman et al. | |
| 9,498,122 B2 | 11/2016 | Friedman et al. | |
| 9,498,642 B2 | 11/2016 | Muller et al. | |
| 9,622,911 B2 | 4/2017 | Rubinfeld et al. | |
| 2001/0016731 A1 | 8/2001 | DeVore et al. | |
| 2001/0022063 A1 * | 9/2001 | Korteweg | A61F 13/38 53/428 |
| 2002/0006394 A1 | 1/2002 | Redmond et al. | |
| 2002/0013577 A1 | 1/2002 | Frey et al. | |
| 2002/0022606 A1 | 2/2002 | Kochevar et al. | |
| 2002/0118338 A1 | 8/2002 | Kohayakawa | |
| 2003/0083649 A1 | 5/2003 | Margaron et al. | |
| 2003/0105521 A1 | 6/2003 | Perez | |
| 2003/0175259 A1 | 9/2003 | Karageozian et al. | |
| 2003/0203839 A1 | 10/2003 | Kruzel et al. | |
| 2003/0208190 A1 | 11/2003 | Roberts et al. | |
| 2004/0137068 A1 | 7/2004 | Bhushan | |
| 2005/0070942 A1 | 3/2005 | Perez | |
| 2005/0090877 A1 | 4/2005 | Harth et al. | |
| 2005/0124982 A1 | 6/2005 | Perez | |
| 2005/0149006 A1 | 7/2005 | Peyman | |
| 2005/0152993 A1 | 7/2005 | De Oliveira | |
| 2005/0241653 A1 | 11/2005 | Van Heugten et al. | |
| 2005/0271590 A1 | 12/2005 | Schwartz et al. | |
| 2005/0283234 A1 | 12/2005 | Zhou et al. | |
| 2006/0074487 A1 | 4/2006 | Gilg | |
| 2006/0084951 A1 | 4/2006 | Heacock et al. | |
| 2006/0106371 A1 | 5/2006 | Muhlhoff et al. | |
| 2006/0134170 A1 | 6/2006 | Griffith et al. | |
| 2006/0166879 A1 | 7/2006 | Bhushan et al. | |
| 2006/0172972 A1 | 8/2006 | Bhushan et al. | |
| 2006/0177430 A1 | 8/2006 | Bhushan et al. | |
| 2006/0206173 A1 | 9/2006 | Gertner et al. | |
| 2006/0235513 A1 | 10/2006 | Price | |
| 2006/0254602 A1 * | 11/2006 | Myer | A61B 90/70 128/898 |
| 2006/0268231 A1 | 11/2006 | Gil et al. | |
| 2006/0275278 A1 | 12/2006 | Choy et al. | |
| 2006/0287662 A1 | 12/2006 | Berry et al. | |
| 2007/0021806 A1 | 1/2007 | Mercier et al. | |
| 2007/0088415 A1 | 4/2007 | Peyman | |
| 2007/0128174 A1 | 6/2007 | Kleinsek et al. | |
| 2007/0129286 A1 | 6/2007 | Zhang | |
| 2007/0135805 A1 | 6/2007 | Peyman | |
| 2007/0142828 A1 | 6/2007 | Peyman | |
| 2007/0156077 A1 * | 7/2007 | Pfister | A61M 35/006 604/2 |
| 2007/0167935 A1 | 7/2007 | Serdarevic | |
| 2007/0207116 A1 | 9/2007 | Brown | |
| 2007/0225778 A1 | 9/2007 | Heacock et al. | |
| 2008/0009901 A1 | 1/2008 | Redmond et al. | |
| 2008/0015660 A1 | 1/2008 | Herekar | |
| 2008/0039769 A1 | 2/2008 | Peyman | |
| 2008/0057023 A1 | 3/2008 | Chynn et al. | |
| 2008/0097174 A1 | 4/2008 | Maynard et al. | |
| 2008/0114283 A1 | 5/2008 | Mattson et al. | |
| 2008/0139671 A1 | 6/2008 | Herekar | |
| 2008/0161780 A1 | 7/2008 | Serdarevic | |
| 2008/0208177 A1 | 8/2008 | Mrochen et al. | |
| 2008/0246920 A1 | 10/2008 | Buczek et al. | |
| 2008/0269119 A1 | 10/2008 | Griffith et al. | |
| 2008/0269730 A1 | 10/2008 | Dotson | |
| 2008/0288063 A1 | 11/2008 | Price, Jr. | |
| 2009/0024117 A1 | 1/2009 | Muller | |
| 2009/0069798 A1 | 3/2009 | Muller et al. | |
| 2009/0099557 A1 | 4/2009 | Sedarevic | |
| 2009/0105127 A1 | 4/2009 | Thompson et al. | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0187178 A1 | 7/2009 | Muller et al. | |
| 2009/0187184 A1 | 7/2009 | Muller | |
| 2009/0192437 A1 | 7/2009 | Soltz et al. | |
| 2009/0209954 A1 | 8/2009 | Muller et al. | |
| 2009/0275923 A1 | 11/2009 | Shimizu et al. | |
| 2009/0275929 A1 | 11/2009 | Zickler | |
| 2010/0057059 A1 | 3/2010 | Makino | |
| 2010/0057060 A1 | 3/2010 | Herekar | |
| 2010/0069894 A1 | 3/2010 | Mrochen et al. | |
| 2010/0087920 A1 | 4/2010 | Marmo | |
| 2010/0094197 A1 | 4/2010 | Marshall et al. | |
| 2010/0094280 A1 | 4/2010 | Muller | |
| 2010/0114109 A1 | 5/2010 | Peyman | |
| 2010/0173019 A1 | 7/2010 | Paik et al. | |

(56) References Cited

U.S. PATENT DOCUMENTS

| | | | |
|---|---|---|---|
| 2010/0179622 A1 | 7/2010 | Wagenaar Cacciola et al. |
| 2010/0185192 A1 | 7/2010 | Muller et al. |
| 2010/0189817 A1 | 7/2010 | Krueger et al. |
| 2010/0210996 A1 | 8/2010 | Peyman |
| 2010/0256705 A1 | 10/2010 | Muller et al. |
| 2010/0286156 A1 | 11/2010 | Pinelli |
| 2010/0312198 A1* | 12/2010 | Guidi .................. A61F 11/006 604/257 |
| 2010/0318017 A1 | 12/2010 | Lewis et al. |
| 2011/0060129 A1 | 3/2011 | Akashi et al. |
| 2011/0060267 A1 | 3/2011 | DeWoolfson et al. |
| 2011/0081323 A1 | 4/2011 | Kleinsek et al. |
| 2011/0086802 A1 | 4/2011 | Dewoolfson et al. |
| 2011/0118654 A1 | 5/2011 | Muller et al. |
| 2011/0125187 A1 | 5/2011 | Soltz et al. |
| 2011/0149247 A1 | 6/2011 | Artsyukhovich |
| 2011/0160710 A1 | 6/2011 | Frey et al. |
| 2011/0237999 A1 | 9/2011 | Muller et al. |
| 2011/0264082 A1 | 10/2011 | Mrochen et al. |
| 2011/0282333 A1 | 11/2011 | Herekar et al. |
| 2011/0288466 A1 | 11/2011 | Muller et al. |
| 2011/0301524 A1 | 12/2011 | Bueler et al. |
| 2011/0306956 A1 | 12/2011 | Islam |
| 2012/0059439 A1 | 3/2012 | Yoon |
| 2012/0065572 A1 | 3/2012 | Lewis et al. |
| 2012/0083772 A1 | 4/2012 | Rubinfeld et al. |
| 2012/0095455 A1 | 4/2012 | Rodmond et al. |
| 2012/0121567 A1 | 5/2012 | Troisi et al. |
| 2012/0203161 A1 | 8/2012 | Herekar |
| 2012/0215155 A1 | 8/2012 | Muller et al. |
| 2012/0238938 A1 | 9/2012 | Herekar et al. |
| 2012/0283531 A1 | 11/2012 | Maynard et al. |
| 2012/0283621 A1 | 11/2012 | Muller |
| 2012/0289886 A1 | 11/2012 | Muller et al. |
| 2012/0303008 A1 | 11/2012 | Muller et al. |
| 2012/0310083 A1 | 12/2012 | Friedman et al. |
| 2012/0310141 A1 | 12/2012 | Kornfield et al. |
| 2013/0060187 A1 | 3/2013 | Friedman et al. |
| 2013/0079759 A1 | 3/2013 | Dotson et al. |
| 2013/0085370 A1 | 4/2013 | Friedman et al. |
| 2013/0131664 A1 | 5/2013 | Muller et al. |
| 2013/0158342 A1 | 6/2013 | Chan et al. |
| 2013/0245536 A1 | 9/2013 | Friedman et al. |
| 2013/0331768 A1 | 12/2013 | Nichamin |
| 2014/0024997 A1 | 1/2014 | Muller et al. |
| 2014/0031845 A1* | 1/2014 | Rynerson ............ A61F 9/00709 606/162 |
| 2014/0368792 A1 | 12/2014 | Friedman et al. |
| 2014/0368793 A1 | 12/2014 | Friedman et al. |
| 2015/0032686 A1 | 1/2015 | Kuchoor |
| 2015/0126921 A1 | 5/2015 | Rubinfeld et al. |
| 2015/0174161 A1 | 6/2015 | Rubinfeld et al. |

FOREIGN PATENT DOCUMENTS

| | | |
|---|---|---|
| CA | 2473703 A1 | 7/2003 |
| CA | 2511217 A1 | 7/2004 |
| CA | 2515720 A1 | 9/2004 |
| CA | 2566961 A1 | 12/2005 |
| CA | 2576308 A1 | 2/2006 |
| CA | 2577025 A1 | 2/2006 |
| CA | 2700884 A1 | 2/2009 |
| DE | 10323422 A1 | 4/2004 |
| JP | 54101440 A | 8/1979 |
| SU | 1803110 A1 | 3/1993 |
| WO | 00/63079 | 10/2000 |
| WO | 0111716 A1 | 2/2001 |
| WO | 2001082933 A2 | 11/2001 |
| WO | 03061518 A2 | 7/2003 |
| WO | 03068247 A1 | 8/2003 |
| WO | 2004024035 A1 | 3/2004 |
| WO | 2005117987 A1 | 12/2005 |
| WO | 2007011874 A2 | 1/2007 |
| WO | 2007011875 A2 | 1/2007 |
| WO | 2007020673 A1 | 2/2007 |
| WO | 2007026382 A1 | 3/2007 |
| WO | 2007035843 A2 | 3/2007 |
| WO | 2007082127 | 7/2007 |
| WO | 2008005059 A1 | 1/2008 |
| WO | 2008055118 A2 | 5/2008 |
| WO | 2009001396 | 12/2008 |
| WO | 2009146151 A2 | 12/2009 |
| WO | 2010023705 | 3/2010 |
| WO | 2010093908 A2 | 8/2010 |
| WO | 2011011202 A1 | 1/2011 |
| WO | 2011019940 A2 | 2/2011 |
| WO | 2011041437 A1 | 4/2011 |
| WO | 2011050164 A1 | 4/2011 |
| WO | 2011056477 A1 | 5/2011 |
| WO | 2011109712 A2 | 9/2011 |
| WO | 2011152861 A2 | 12/2011 |
| WO | 2012035403 A1 | 3/2012 |
| WO | 2012047307 A1 | 4/2012 |
| WO | 2013148895 A1 | 10/2013 |
| WO | 2013148896 A1 | 10/2013 |
| WO | 2013158611 A1 | 10/2013 |
| WO | 2014071408 A1 | 5/2014 |

OTHER PUBLICATIONS

International Search Report and Written Opinion for PCT/US2013/034187 dated Jul. 22, 2013 in 21 pages.

Rose, R.C. et al., Ocular oxidants and antioxidant protection, Experimental Biology and Medicine, 1998, vol. 217, No. 4, pp. 397-407.

Beijing Yasi Technology and Development Co., Ltd."Eye sponge product information", Jul. 29, 2011, in 2 pages.

International Search Report and Written Opinion for PCT/US2015/029011 dated Aug. 3, 2015 in 14 pages.

Shinichi Ibuski et al., "Photochemically Cross-Linked Collagen Gels as Three-Dimensional Scaffolds for Tissue Engineering," Tissue Engineering, Nov. 8, 2007, vol. 13, No. 8, Mary Ann Liebert, Inc.

Third Party Observation for European application No. 13767439.6 submitted to the European Patent Office on Nov. 30, 2018, 2 pages.

Hafezi, Cross-Linking of Corneal Collagen with UVA and Riboflavin for the Treatment of Corneal Disease, 2009, Iranian Journal of Ophthalmology, vol. 21, No. 2, pp. 3-12.

Letko et al. UVA-light and Riboflavin-mediated Corneal Collagen Cross-linking, 2011, International Ophthalmology Clinics, www.internat-ophthalmology.com, pp. 1-14.

Extended European Search Report for European application No. 18182071.3 dated Oct. 2, 2018 in 6 pages.

Rieger, et al. "The Effect of Iodide Iontophoresis on the Antioxidative Capacity of the Tear Fluid" Graefe's Archive for Clinical Experimental Ophthalmology. 248:1639-1646 (2010).

Supplementary European Search Report for EP 13767439.6 dated Sep. 15, 2015 in 6 pages.

Horwath-Winter J, et al: "Iodide iontophoresis as a treatment for dry eye syndrome", The British Journal of Ophthalmology, Jan. 2005, pp. 40-44, vol. 89, No. 1.

Singh et al: "Clinical Evaluation of Sodium Iodide in the Treatment of Various Types of Cataracts", Journal of the Indian Medical Association, 1983, pp. 119-121, vol. 81, No. 7-8.

Winkler et al: "Effect of Iodide on Total Antioxidant Status of Human Serum", Cell Biochemistry and Function, Jun. 2000, pp. 143-146, vol. 18, No. 2.

Partial supplementary European Search Report for EP 13768403.1 dated Oct. 23, 2015 in 10 pages.

Ilens Ophthalmic Solution, http://naikutty.in/medicine-list-i/article/86937-ilens-solution, Date unknown but available prior to the date of this application, access date Dec. 22, 2015.

J. Wernli, S. Schumacher, E. Spoerl, and M. Mrochen, "The efficacy of corneal cross-linking shows a sudden decrease with very high intensity UV light and short treatment time," Investigative Ophthalmology and Visual Science, vol. 54, No. 2, pp. 1176-1180, Feb. 2013.

(56) References Cited

OTHER PUBLICATIONS

R. R. Krueger, E Spoerl, and S. Herekar, "Rapid vs standard collagen CXL with equivalent energy dosing," in Proceedings of the 3rd International Congress of Corneal Collagen Cross-Linking, Zurich, Switzerland, Dec. 2007.
Pavel Kamaev, et al,. "Photochemical kinetics of corneal cross-linking with Riboflucin", Investigative Ophthalmology and Visual Science, Apr. 2012, vol. 53, No. 4, 2360-2367.
Extended European Search Report dated Oct. 19, 2016 for related EP Patent Application No. 14775693.6 in 8 pages.
International Search Report and written opinion dated Jan. 17, 2012 for PCT/US2011/033873.
Olson, "Control lamp flora in developed caves" Heldreth-Werker V. & Werker J.C. Cave Conservation and Restoration, Huntsville: National Speleolgical Society: 343-348.
Baert, et al "Medical Radiology: Diagnostic Imaging, Radiological Imaging of the Ureter, copyright 2003, Springer" (Joffre, et all.) DOI https://doi.org/10.1007/978-3-642-55831-3.
Abraxis (Iodopen MSDS, Revision date of Jun. 13, 2006).
International Preliminary Report on patentability for PCT/US2013/034185, dated Oct. 1, 2014, in 7 pages.
Harvey, et al. "Formulation and stability of a novel artificial human sweat under conditions of storage and use" Toxicology in Vitro, 2010, vol. 24, pp. 1790-1796.
International Preliminary Report on patentability for PCT/US2013/034467, dated Oct. 1, 2014, in 6 pages.
Extended European Search Report issued in EP18196714.2 dated Jan. 30, 2019 in 8 pages.
El-Raggal (Riboflavin-Ultraviolet A Corneal Cross linking for Keratoconus, Middle East Afr. J. Ophthalmol. Oct.-Dec. 2009; 16(4):256-259).
Bessonova, et al., "A study of the stability of eye drops containing riboflavine (Russian)." XP002719481. Database accession No. EMB-1978057912. Abstract Elseview Science Publishers, Amsterdam, NL 1977.
Elstner, et al. "Uptake and biochemical activity of potassium iodide in isolated rabbit eyes." XP008167001. Phtlalmologica 191(2):122-126 (1985). English Abstract.
Koltun, et al. "improving the production technology of vitamin-containing eye drops to ensure their microbiological purity." CP00271948, Database accession No. PREV199497454025. Abstract Biosciences information service, Philadelphia, PA, 1993.
Rieger, "Anti-oxidtaive capacity of various articifial tear prepartions." XPO003014992, Graefe's Archive for Clinical Experimental Ophthalmology. 239:222-226 (2001).
Schmut, et al. "Iodide protection from UVB irradiation-induced degradation of hyaluronate and against UVB-damaage of human conjunctival fibroblasts." Graefe's Arch Clin Exp Ophthalmol 242:279-283 2004.
Shimmura, et al. " Subthershold UV radiation-induced peroxide formation in cultured coreal epithelial cells: the protective effects of lactoferrin" Exp. Eye Res. 63: 519-526 1996.
Ishimitsu "The photochemical decomposition and hydroxylation of phenylalanine in the presence of riboflavin" Chem. Pharm. Bul. 33(4): 1552-1556 1985.
Zhang, et al. "Clinical effect of traditional Chinese herb combined with sodium iodide in treating corneal opacity." XP-002719483, International Journal of Ophthalmology, 7: 217-219, 2007.
Extended European Search Report dated Feb. 10, 2014 for related EP Patent Application No. 11831060 in 15 pages.
Cho et al. "Reactive Oxygen Species-Induced Apoptosis and Necrosis in Bovine Corneal Endothelial Cells." Investigative Ophthalmology & Visual Science. 40(5):911-919, Apr. 1999.
Fujimori. "Cross-linking and fluorescence changes of collagen by glycation and oxidation." Biochimica et Biophysica Acta. 998:105-110, 1989.
Hull et al. "Hydrogen Peroxide-Mediated Corneal Endothelial Damage." Investigative Ophthalmology & Visual Science. 25:1246-1253, 1984.
Iseli et al. "Efficacy and Safety of Blue-light Scleral Cross-linking." International Congress of Corneal Cross-linking, Dec. 7-8, 2007; Zurich, Switzerland. pp. S752-S755.
Khadem et al. "Photodynamic Biologic Tissue Glue." Cornea. 13(5):406-410, 1994.
Kohlhaas et al. "Biomechanical evidence of the distribution of cross-links in corneas treated with riboflavin and ultraviolet A light." J Cataract Refract Surg. 32:279-283, Feb. 2006.
Krueger et al. "Rapid vs Standard Collagen CXL with Equivalent Energy Dosing." Third International Congress of Corneal Cross-linking. Dec. 7-8, 2007; Zurich, Switzerland, in 25 pages.
Sato et al. "The Primary Cytotoxicity in Ultraviolet-A-Irradiated Riboflavin Solution is Derived from Hydrogen Peroxide." The Society for Investigative Dermatology, Inc. 105(4):608-612, Oct. 1995.
Seiler et al. "Corneal Cross-Linking-Induced Stromal Demarcation Line." Clinical Science. 25(9):1057-1059, Oct. 2006.
Spoerl et al. "Increased resistance of cross-linked cornea against enzymatic digestion." Current Eye Research. 29(1):35-40, 2004.
Spoerl et al. "Induction of Cross-links in Corneal Tissue." Exp. Eye Res. 66:97-103, 1998.
Spoerl et al. "Safety of UVA-Riboflavin Cross-Linking of the Cornea." Cornea. 26(4):385-389, May 2007.
Spoerl et al. "Thermo-mechanical Behavior of Collagen-Cross-Linked Porcine Cornea." Ophthalmologica. 218:136-140, 2004.
Wollensak et al. "Collagen Fiber Diameter in the Rabbit Cornea After Collagen Cross-linking by Riboflavin/UVA." Cornea. 23(5):503-507, Jul. 2004.
Wollensak et al. "Corneal Endothelial Cytotoxicity of Riboflavin/UVA Treatment in vitro." Ophthalmic Res. 35:324-328, 2003.
Wollensak et al. "Endothelial cell damage after riboflavin-ultraviolet-A treatment in the rabbit." J Cataract Refract Surg. 29:1786-1790, 2003.
Wollensak et al. "Keratocyte Apoptosis After Corneal Collagen Cross-linking Using Riboflavin/UVA Treatment." Cornea. 23(1):43-49, Jan. 2004.
Wollensak et al. "Keratocyte cytotoxicity of riboflavin/UVA treatment in vitro." Eye. 2004, in 5 pages.
Wollensak et al. "Long-term biomechanical properties of rabbis cornea after photo-dynamic collagen cross-linking." Acta Ophthalmologica. 87:48-51, 2009.
Wollensak et al. "Riboflavin/Ultraviolet-A-induced Collagen Crosslinking for the Treatment of Keratoconus." Am J Ophthalmol. 135:620-627, 2003.
Wollensak et al. "Stress-strain measurements of human and porcine corneas after riboflavin-ultraviolet-A-induced cross-linking." J Cataract Refract Surg. 29:1780-1785, 2003.
Wollensak et al. "Wound Healing in the Rabbit Cornea After Corneal Collagen Cross-Linking With Riboflavin and UVA." Cornea. 26:600-605, 2007.
International Search Report and Written Opinion for related international application No. PCTUS2013/034185, dated Jul. 11, 2013, in 10 pages.
International Search Report and Written Opinion for related international application No. PCTUS2013033923, dated Jul. 12, 2013, in 11 pages.
Epstein."Refraktive Chirurgie." Therapeutische Umschau. Revue Therapeutique. 66(3):207-210 (Mar. 2009). English abstract.
Chuo et al. "Modem Corneal and Refractive Procedures." Expert Review of Ophthalmology. 6(2):247-266 (Apr. 2011).
Kullman. "Alternative Applications of the Femtosecond Laser in Ophthalmology." Seminars in Ophthalmology. 25(5-6):256-264 (Nov. 2010).
Kohnen et al. "Bewertung und Qualitatssicherung refraktiv-chirurgischer Eingriffe durch die DOG und den BVA (Evaluation and quality assurance of refractive surgery by the German Ophthalmological Society and the Professional Association of German Ophthalmologists)." Ophthalmologie. 108(9):869-882 (Sep. 2011). Available only in German.
Kato et al. "Topography-Guided Conductive Keratoplasty: Treatment for Advanced Keratoconus." American Journal of Ophthalmology. 150(4):481-489 (Oct. 2010).

(56) References Cited

OTHER PUBLICATIONS

Oduntan et al. "A review of the role of oxidative stress in the pathogenesis of eye diseases." S Afr Optom. 70(4):191-199 (2011).
Gilgun-Sherki et al. Oxidative stress induced neurodegenerative diseases: the need for antioxidants that penetrate the blood brain barrier, Neuropharmacology 40: 959-975, 2001.
Bickers et al. "Oxidative Stress in the Pathogenesis of Skin Disease." The Society for Investigative Dermatology. pp. 2565-2575, 2006.
Sukkar et al. "Oxidative stress and nutritional prevention in autoimmune rheumatic diseases." Autoimmunity Reviews. 3:199-206 (2004).
Uttara et al. "Oxidative Stress and Neurodegenerative Diseases: A Review of Upstream and Downstream Antioxidant Therapeutic Options." Current Neuropharmacology. 7:65-74 (2009).
Wells et al. "Oxidative Stress in Developmental Origins of Disease: Teratogenesis, Neurodevelopmental Deficits, and Cancer." Toxicological Sciences. 108(1):4-18 (2009).
EMX Industries, Inc.; ColoMax HEX color sensors; Mar. 2010.
International Search Report and Written Opinion for related PCT/US2014/024770 dated Aug. 6, 2014 in 17 pages.
Wollensak et al., "Cross-linking of scleral collagen in the rabbit using riboflavin and UVA", ACTA Ophthalmologica Scandinavica, 2005, vol. 83, pp. 477-482.
International Search Report and Written Opinion for related international application No. PCT/US2013/034467 dated Jul. 26, 2013 in 12 pages.
Agbor, et al. "Effect of Iodine Supplementation on Antioxidant Status of Normal and Alloxan Monohydrate in Toxicated Rats", International Journal of Pharmacology, 7 (6): pp. 726-731, 2011, Asian Network for Scientific Information.

\* cited by examiner

OPHTHALMIC TREATMENT SOLUTION DELIVERY DEVICES AND DELIVERY AUGMENTATION METHODS

BACKGROUND

Collagen cross-linking is a treatment for multiple ophthalmic disorders. In some cases, collagen cross-linking may also be combined with other treatments to improve corneal strength or optical refraction, such as corneal ring segment inserts, topography-guided laser, and the like. Corrective lenses are normally required after these treatments for weakened corneas, but with smaller, more normalized prescriptions. Increased corneal symmetry allows for more comfortable contact lens wear, often of daily disposable lenses. Collagen cross-linking limits deterioration of vision, increases unaided and uncorrected vision, and may reduce the need for corneal transplantation. Collagen cross-linking may also have a role in stabilizing and "locking in" refractive effects of other procedures.

SUMMARY

Disclosed herein, in certain embodiments, is a method of applying an ophthalmic composition to an eye, comprising applying the ophthalmic composition after preparing the epithelium of an eye for more effective treatment. In some embodiments, the method comprises preparing the epithelium of the eye by rubbing or contacting the eye with a first sponge device, so as to manipulate or "buff" the tissue of the epithelium. In some embodiments, the method comprises preparing the epithelium of the eye by rubbing the eye with the first sponge device in a circular pattern. In some embodiments, the method comprises removing lipids, mucus and microvilli. In some embodiments, the first sponge device comprises a handle with a sponge attached to one end of the handle for contacting the eye. In some embodiments, the sponge is dry or pre-wetted with an ophthalmic composition. In some embodiments, the sponge is pre-wetted with a riboflavin composition, artificial tears, or a combination thereof. In some embodiments, use of the first sponge device to prepare the epithelium markedly increases the permeability of the epithelium to medications or ophthalmic solutions applied to the surface of the epithelium after preparation or polishing with the buffing or polishing sponge.

In some embodiments, the method further comprises applying the ophthalmic composition with a second, loading sponge or sponge device. In some embodiments, the method further comprises placing the second sponge or sponge device over the eye to act as a depot or reservoir for holding the ophthalmic composition or solution in contact with the eye surface over an area where the solution needs to be absorbed into the eye.

In certain embodiments, the second sponge device comprises a round, loading sponge which peri- or pre-operatively covers all or a portion of the eye surface. In some embodiments, the size of the loading sponge does not exceed the eye surface. In some embodiments, the diameter of the sponge is about 3 mm. to about 12 mm. In some embodiments, the second sponge device has a diameter of around 11.5 mm and may be pre-formed to follow the curvature of most or all of the exposed, curved surface of the eye or may be of flexible material designed to adopt the shape of the exposed, curved surface of the eye. In some embodiments, the second sponge device or loading sponge may be pre-saturated with an ophthalmic solution. In some embodiments, the second sponge device may be placed on the eye surface and solution can be dripped onto the sponge device after placement. In some embodiments, the ophthalmic solution may comprise 0.2% to 10.0% by weight riboflavin in an aqueous carrier, and optionally, sodium iodide, catalase, artificial tears, or any combinations thereof.

Disclosed herein, in certain embodiments, is a first or preparation sponge device for use in manipulation of tissue on the surface of an eye prior to application of the second sponge device or loading sponge. The first, preparation sponge device comprises a preparation sponge having a tissue preparation surface shaped for manipulating and rubbing across the surface of an eye. In some embodiments, the preparation sponge has little or no risk of disrupting or perforating the epithelium. In some embodiments, the first sponge device further comprises a handle operatively connected to the preparation sponge. In some embodiments, the first sponge device may be a spherical or part spherical sponge without a handle, and may be held by forceps or similar instruments during preparation of the eye surface. In some embodiments, at least the tissue preparation surface of the sponge is round or at least partially round. In some embodiments, at least the tissue preparation surface of the sponge does not have sharp edges. In some embodiments, the tissue preparation surface of the sponge is rounded. In some embodiments the sponge of the first sponge device is of part circular shape. In some embodiments, the sponge may have a straight edge or other shaped edge attached to the handle. In some embodiments, the preparation sponge is made of a cellulose sponge material. In some embodiments, the preparation sponge is made of polyvinyl acetate (PVA) sponge material. In some embodiments, the preparation sponge is wetted with an ophthalmic solution prior to use in preparation of the eye surface. In some embodiments, the ophthalmic solution is 0.2% to 10.0% by weight riboflavin in an aqueous carrier, and optionally, sodium iodide, catalase, artificial tears, or any combinations thereof.

Use of the first, preparation sponge device followed by the second sponge device or loading sponge may augment or enhance delivery of any ophthalmic treatment solution to the eye for use in photochemical treatment of the cornea or for other types of treatment, such as application of eye medications such as glaucoma medications or anti-inflammatory medications such as steroids. In certain embodiments, the treatment solution is a riboflavin solution.

Disclosed herein, in certain embodiments, are sponges that improve the passage or penetration of riboflavin or other ophthalmic drugs through the epithelial barrier to avoid the surgical complications that arise from de-epithelialization, which can result in more disruption of the tissue than is necessary for the procedure to be effective. The reduction in patient discomfort combined with more rapid restoration of visual acuity make a trans-epithelial procedure better for the patient. In some embodiments, the first and second sponge devices are sterile. In some embodiments, the preparation sponge is part circular shape when dry and is configured to absorb liquid and expand into a spherical or part-spherical shape when wetted. In some embodiments, the preparation sponge is spherical or part-spherical in its dry condition. The preparation sponge may be of cellulose, PVA, or urethane sponge material. The first sponge device or preparation sponge has little or no risk of disrupting or perforating the epithelium, resulting in as little disruption of the epithelium as possible while still increasing penetration of the riboflavin or other solution into the deeper layers of the cornea without disrupting or causing any significant epithelial defects in the corneal surface.

In some embodiments, the first or preparation sponge device is of sponge or other sponge-like materials designed to enhance epithelial permeability by gently removing lipids, mucus, and dead surface epithelial cells. In some embodiments, the preparation sponge is packaged along with a blunt plastic shaft or other tool to assist in "twirling" this sponge around on the cornea or sclera or other parts of the eye to manipulate the tissue to be treated in an effort to enhance penetration of the riboflavin or other solution into the eye.

Further disclosed herein, in certain embodiments, is a method of using a first sponge device or preparation sponge as disclosed herein to improve the penetration of riboflavin or other ophthalmic drugs through the epithelial barrier to avoid the surgical complications that arise from de-epithelialization, which in some embodiments result in more disruption of the tissue than is necessary for the procedure to be effective. The reduction in patient discomfort combined with more rapid restoration of visual acuity make a trans-epithelial procedure better for the patient. In some embodiments, the preparation sponge is rubbed gently over the surface of the eye in a circular pattern after application of a topical anesthetic, in order to prepare the epithelium for improved penetration of riboflavin or other solutions. In some embodiments, the method removes lipids, mucus, microvilli and other natural barriers to riboflavin or other ocular solutions loading into the deeper ocular tissues. In some embodiments, it is possible that this preparation may produce very fine micro-abrasion to allow the riboflavin solution to penetrate through the epithelium into the cornea more easily, but this is not essential and may not occur in all cases. In some embodiments, the method has little or no risk of disrupting or perforating the epithelium resulting in as little disruption of the epithelium as possible while still increasing penetration of the riboflavin or other solution into the deeper layers of the cornea. In some embodiments, the method further comprises applying an ophthalmic solution (e.g., a riboflavin solution) to the eye in any suitable manner. In some embodiments, the ophthalmic solution is applied through a second, loading sponge placed over the eye to act as a depot or reservoir for the ophthalmic solution, since the tear film itself is only about 5 microns thick, which offers only a very small reservoir of riboflavin solution. This also moisturizes the corneal surface.

In various embodiments, the sponge device is used in one or more microsurgical ophthalmic procedures for tissue manipulation and management of fluids. In other embodiments, the sponge device is used in one or more microsurgical ophthalmic procedures for the management of one or more fluids. In some embodiments, the sponge device is placed on the cornea to moisten the cornea during one or more microsurgical procedures.

The above devices and methods may be used in various microsurgical ophthalmic procedures, including preparation of the epithelium for loading of one or more fluids through the epithelium into the eye for photochemical or other treatment.

Other features and advantages of the present disclosure will become more readily apparent to those of ordinary skill in the art after reviewing the following detailed description and accompanying drawings.

BRIEF DESCRIPTION OF THE DRAWINGS

The details of the present disclosure, both as to its structure and operation, may be gleaned in part by study of the accompanying drawings, in which like reference numerals refer to like parts, and in which.

DETAILED DESCRIPTION

Certain embodiments as disclosed herein provide for ocular treatment solution delivery devices and delivery augmentation methods. For example, according to embodiments of the disclosure, devices and methods are provided for preparing the corneal epithelium for better penetration of riboflavin solutions or other ophthalmic solutions into the cornea.

A popular treatment of corneal diseases, including keratoconus, post-LASIK ectasia, and pellucid marginal degeneration, involves the removal of the epithelium followed by administration of a riboflavin solution and irradiation by ultraviolet-A light. Riboflavin acts as a photosensitizer and facilitates the cross-linking of stromal collagen fiber which prevents further disease progression. However, the removal of the epithelium carries numerous risks for the patient, including post-operative pain, infection risk, delayed wound healing, corneal perforation, stromal haze, and herpetic keratitis. Therefore, it would be safer to treat the patient without having to surgically remove the epithelium. Unfortunately, there are many obstacles to this approach because the intact epithelium prevents the cornea from rapidly and conveniently absorbing the riboflavin solution. This invention discloses novel devices and methods for allowing convenient treatment of corneal diseases with medications or with ophthalmic solutions such as riboflavin solutions without removing the epithelium, and may increase the effectiveness of such treatments.

After reading this description it will become apparent to one skilled in the art how to implement the disclosure in various alternative embodiments and alternative applications. However, although various embodiments of the present disclosure will be described herein, it is understood that these embodiments are presented by way of example only, and not limiting. As such, this detailed description of various alternative embodiments should not be construed to limit the scope or breadth of the present disclosure as set forth in the appended claims.

The time period for sufficient riboflavin to penetrate into the cornea when the solution is applied in drops to the eye without removal or treatment of the epithelium layer can be one to three hours. This is a problem for both patients undergoing treatment and for surgeons, in view of the extended time period needed. In some embodiments described below, eye surface preparation or manipulation reduces the initial time needed for an ophthalmic solution (e.g., a riboflavin solution or other ophthalmic solution) to penetrate sufficiently into the cornea in as little as seven to eleven minutes without requiring removal of the epithelium, significantly reducing patient discomfort and the time needed to complete the treatment.

Manipulation of the epithelium prepares it for improved penetration of the epithelium by the ophthalmic solution (e.g., a riboflavin solution), without having to remove the epithelium altogether. The cornea absorbs the riboflavin well until the corneal stroma is sufficiently loaded.

FIGS. 1 to 10 illustrate an exemplary device and method for improving the penetration of riboflavin or other ophthalmic solutions or fluids through the epithelial barrier, while avoiding the surgical complications that arise from deepithelialization. The reduction in patient discomfort, the more rapid restoration of visual acuity, and the reduced risk of infection or stromal haze make a trans epithelial procedure better for the patient.

Figure 1:
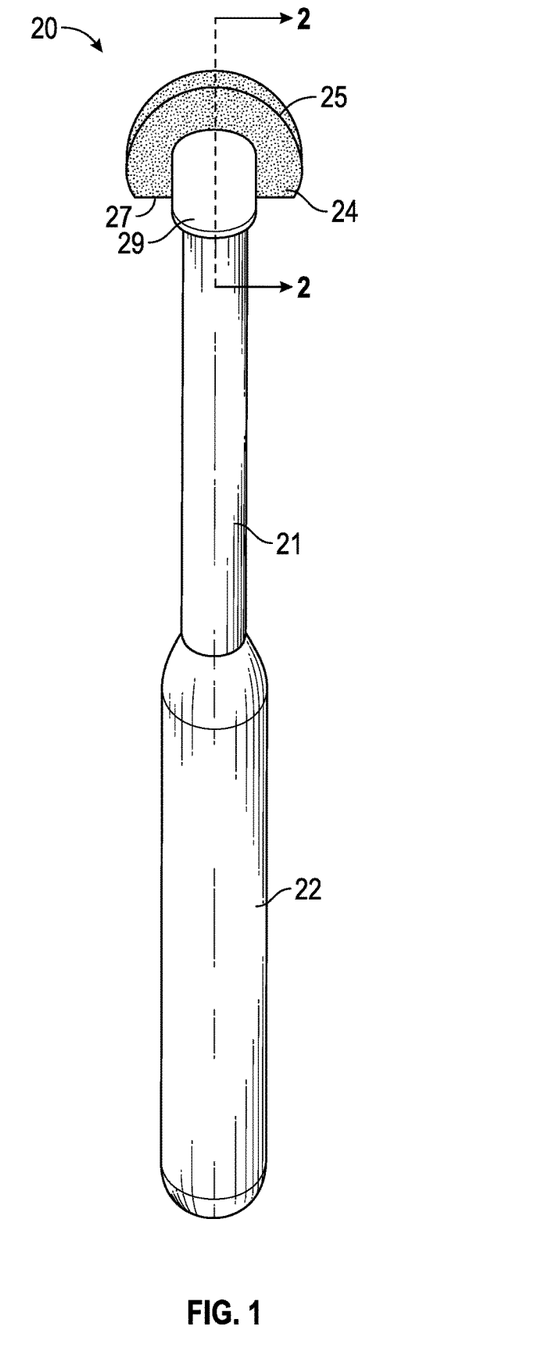
FIG. 1 exemplifies an enlarged perspective view of one embodiment of a preparation or tissue manipulating sponge device for use in preparing the corneal epithelium for subsequent application of an ocular treatment solution to the eye.
Figure 8:
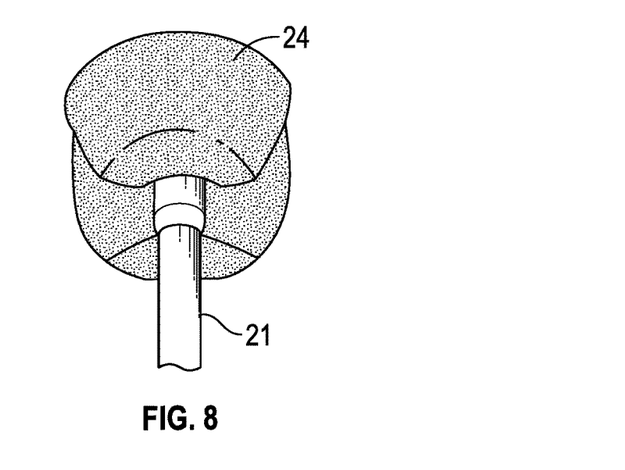
Figure 9:
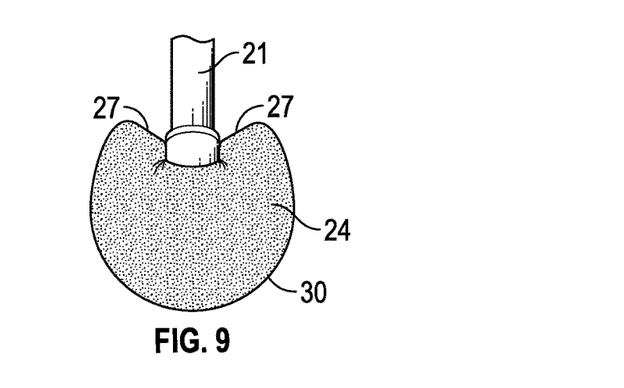
Figure 10:
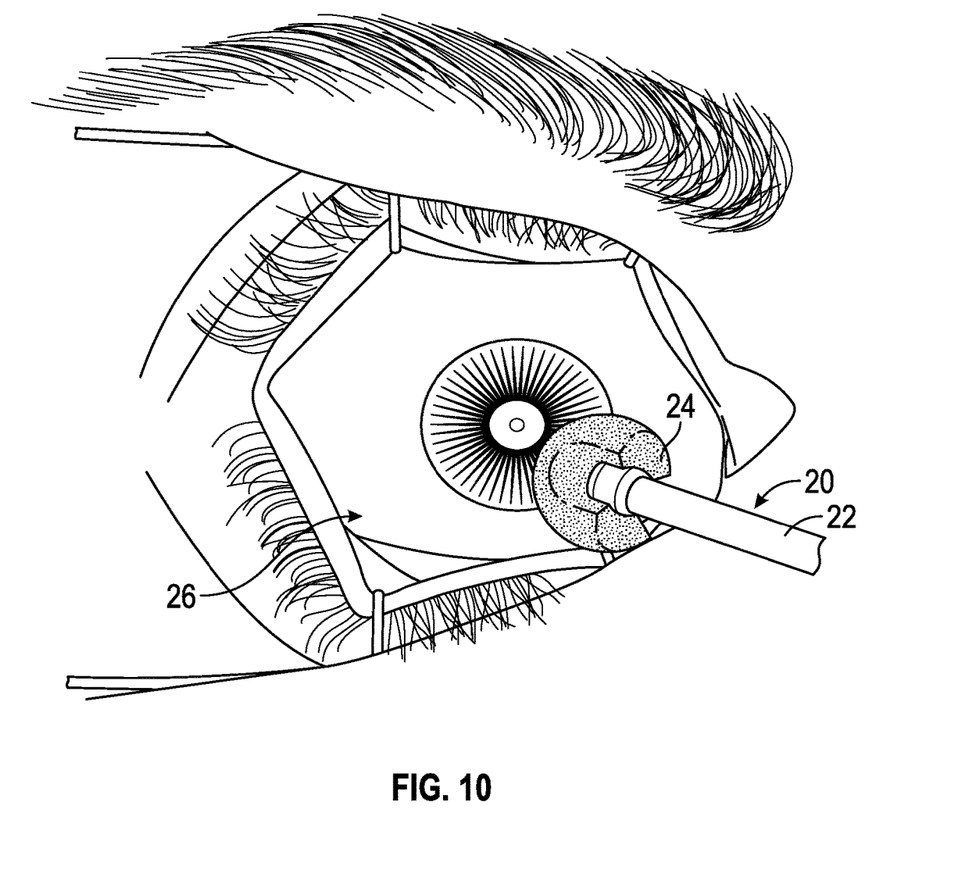
FIG. 10 illustrates an exemplary use of the sponge of FIGS. 1 to 9 to manipulate the corneal surface in a swirl action.

In some embodiments, a first or preparation sponge device 20 as illustrated in FIG. 1-9 is rubbed gently over the surface of the eye 26 after application of a topical anesthetic, as illustrated in FIG. 10. The sponge may be rubbed gently in a circular or swirling manner, in order to manipulate the eye surface, in other words to "buff" or "polish" the eye to a dull sheen. In one embodiment, preparation sponge device 20 comprises an elongate handle or shaft 21 with a gripping portion 22 at one end and a sponge head 24 of relatively rigid sponge material attached to the other end of shaft 21, as illustrated in FIG. 1. When dry, the head 24 of this embodiment is a generally flat, part-circular or part disk shaped piece of surgical or medical grade sponge material such as relatively rigid, highly absorbent natural cellulose or highly absorbent, fast wicking polyvinyl acetate (PVA) material or the like, for example Ultracell® PVA or other sponge materials used in Weck-Cel® fluid control medical sponges as manufactured by Beaver-Visitec of Waltham, Mass. The handle shaft 21 may be of any suitable material, such as injection molded plastic material, and may be transparent or opaque.

Figure 2:
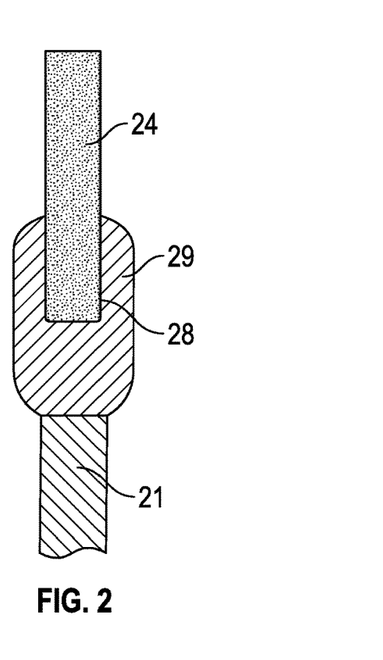
FIG. 2 is a cross section on the lines 2-2 of FIG. 1.
Figure 3A:
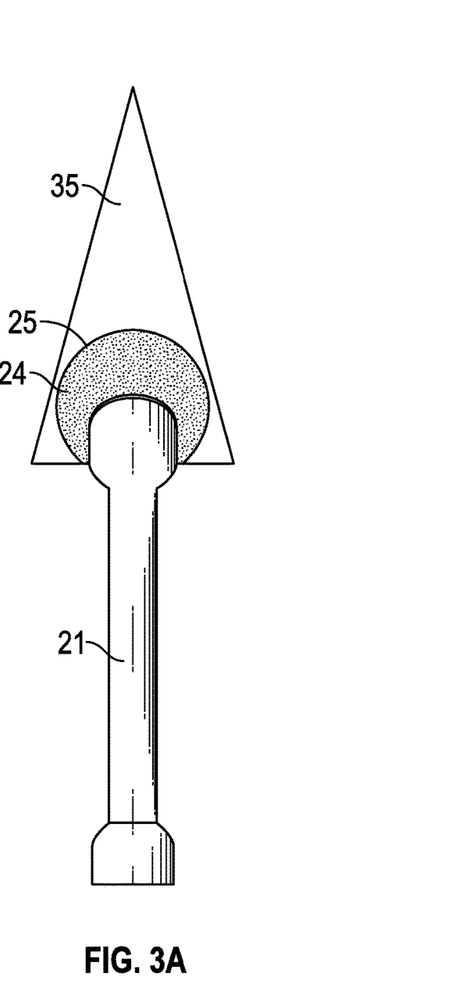
FIG. 3A is a top plan view of a spear shaped sponge attached to the handle of FIGS. 1 and 2 prior to cutting the sponge into the rounded shape of FIGS. 1 and 2, according to one example of a method of making the preparation sponge device of FIGS. 1 and 2.
Figure 3B:
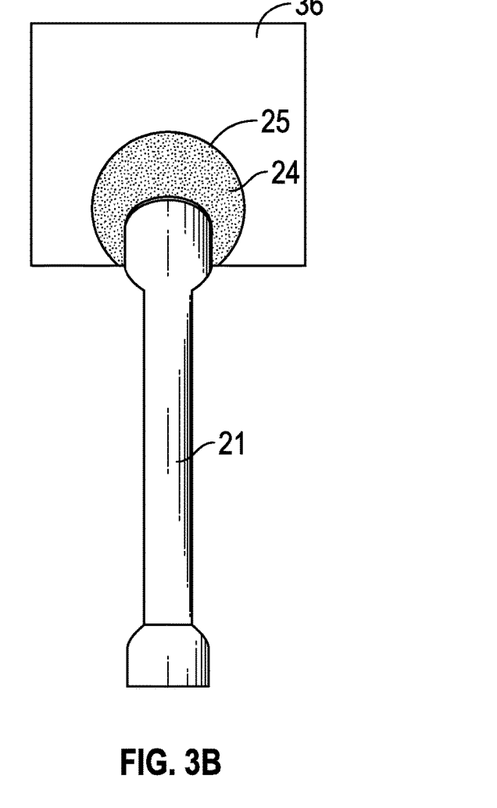
FIG. 3B is a top plan view of a sponge blank attached to the handle of FIGS. 1 and 2 prior to cutting the sponge into the rounded shape of FIGS. 1 and 2, according to another example of a method of making the preparation sponge device of FIGS. 1 and 2
Figure 4:
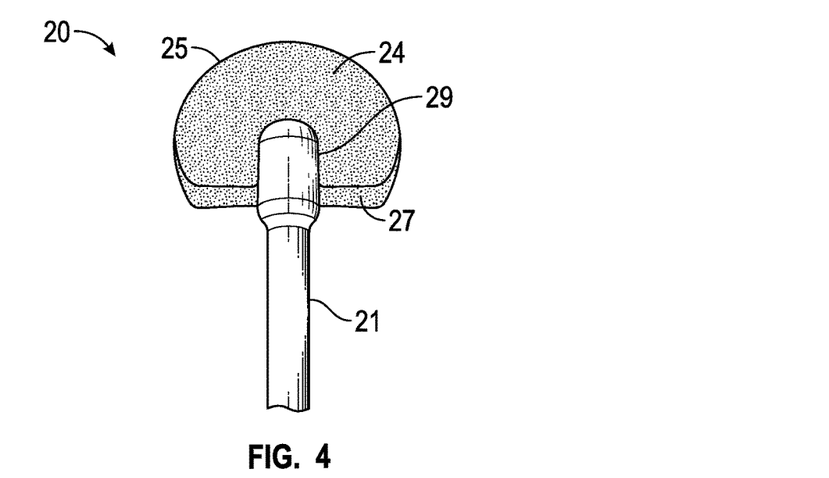
FIG. 4 is a cut away top perspective view of the tissue preparation sponge device of FIGS. 1 to 3, showing the sponge head with part of the handle cut away, with the sponge head in a dry condition.
Figure 5:
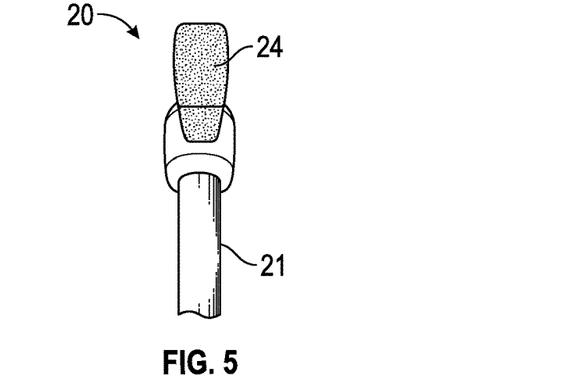
FIG. 5 is a side elevation view of the preparation sponge device of FIGS. 1 to 4, with the handle partially cut away as in FIGS. 2 and 4.
Figure 6:
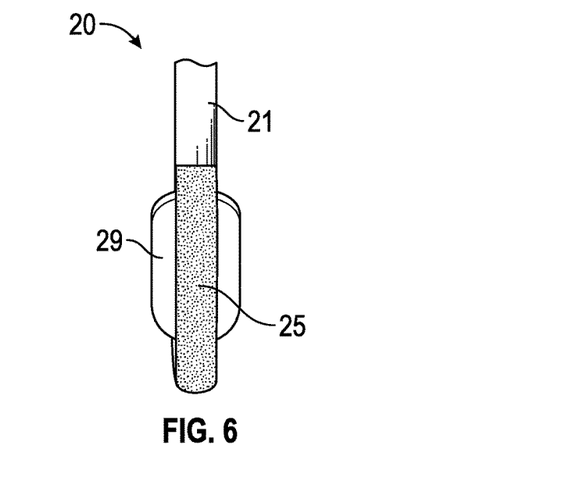
FIG. 6 is a top end perspective view of the preparation sponge device of FIGS. 1 to 5, with the handle partially cut away as in FIGS. 4 and 5.

Sponge 24 has a rounded edge or rim 25 and a straight edge or rim 27, and is held at the center of the straight edge in recess 28 between spaced claws or end portions 29 of the shaft 21, as illustrated in FIG. 2. Sponge 24 may be secured in recess 28 via adhesive or the like. FIGS. 3A and 3B illustrate some alternative methods for manufacture of the preparation sponge device 20. The manufacturing method may be similar to that for conventional spear shaped medical sponges. In FIG. 3A, a spear shaped sponge 35 is secured to handle 21, and sponge 35 is then cut along line 25 to form part circular sponge 24. The thus-formed rounded edge or rim 25 forms more than half of the periphery of a circle, as can be seen in FIG. 3A. In FIG. 3B, a sponge blank 36 is attached to handle 21, and is cut along line 25 to form the part-circular sponge 24. In each case, the rounded edge 25 passes the half way or semi-circle point and starts to curve back in towards the handle, as illustrated in FIGS. 1 and 4. The thickness of the sponge may be around 1 mm while the diameter of the part circular sponge may be in the range from 4.5 mm to around 8 mm. In one example, the diameter of the part-circular edge was about 6.5 mm.

Figure 7:
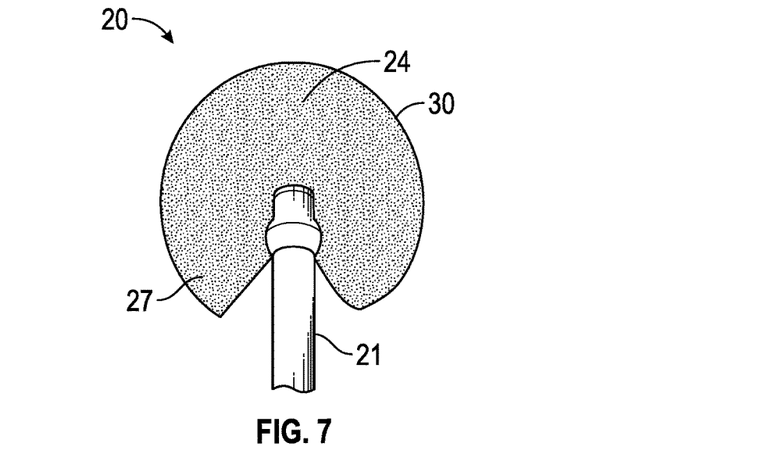
FIGS. 7 to 9 are cut away views of the preparation sponge device corresponding to the views of FIGS. 4 to 6 but with the sponge head in a wet, expanded condition.

FIGS. 1, 2 and 4 to 6 illustrate the sponge device 20 from different directions, with the sponge 24 in a dry, unexpanded state. When the sponge is wetted, the sponge material swells and continues to swell until it creates a rounded ball-like or substantially spherical shape, as illustrated in FIGS. 7 to 9. The handle attachment at the center of the sponge restricts the central portion from swelling, while allowing the remainder of the sponge to swell or expand freely, creating eye preparation surfaces 30 which are all rounded when the sponge is sufficiently wetted, as seen in FIGS. 7 to 9. Because the sponge comprises more than half of a circle and the straight edge 27 of the sponge faces towards the handle when the device is in use, the straight edges on each side of the attachment area are moved away from the treatment area as the sponge device is wetted and expands, forming a generally V-shape as seen in FIGS. 7 and 9. This moves edge surfaces away from the treatment area and avoids the risk of an edge surface contacting the eye.

In some embodiments, the sponge 24 is pre-wetted prior to use so that it is in the expanded condition of FIGS. 7 to 9 before contacting the eye. Once wetted, the material has a softness and roundness that reduces the risk of causing epithelial defects when rubbing gently over the epithelial surface of the eye, as illustrated in FIG. 10. In other embodiments, the sponge may not be pre-wetted prior to use, but starts swelling and rounding up when touched to the tear meniscus from contact with eye fluids, so that it softens prior to the eye surface preparation procedure.

In some embodiments, rubbing or buffing the epithelium gently with the expanded sponge 24 removes lipids, mucus and microvilli as well as dead epithelial cells which would otherwise resist penetration of fluid through the epithelium. In some embodiments, the wet sponge is rubbed gently over the surface of the eye, for example in a circular pattern. In some embodiments, a topical anesthetic is applied to the eye before the application and use of the wet sponge.

Figure 11A:
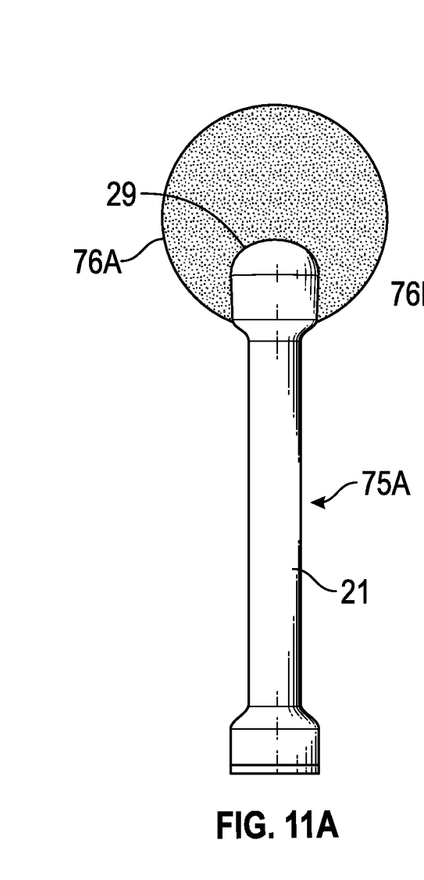
FIGS. 11A to 11C are top plan views illustrating some other embodiments of the buffing or polishing sponge device with a sponge head of circular shape.
Figures 11B, 11C:
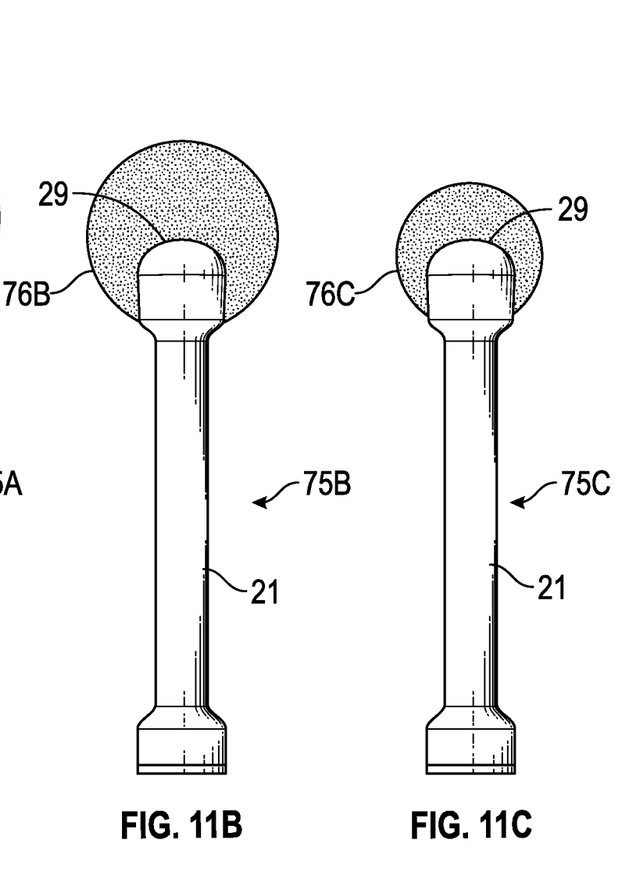

FIGS. 11A to 11C illustrate modified sponge devices 75A, 75B and 75C, respectively, which are similar to the sponge device of FIGS. 1 to 9, but have a completely circular head 76A, 76B, 76C attached to handle 21 instead of a part circular head with a straight lower edge as in the first embodiment. In some embodiments, the head diameters in FIGS. 11A to 11C are around 8 mm, 6.5 mm, and 4.5 mm, respectively, and the dry sponge head has flat opposite faces as in the first embodiments. When wetted, the sponge heads of FIGS. 11A to 11C also expand to a substantially spherical shape. Modified sponge device 78 of FIG. 12 has a spherical head 80 of expanded foam material. This device is ready to use with a completely rounded surface, and absorbs liquid at a faster rate than the dry, compressed foam heads of the previous embodiments. Head 80 may be made of urethane sponge material, for example. This sponge device maintains structural rigidity for preparation of the epithelium for penetration of riboflavin solutions or other solutions or medications.

Figure 12:
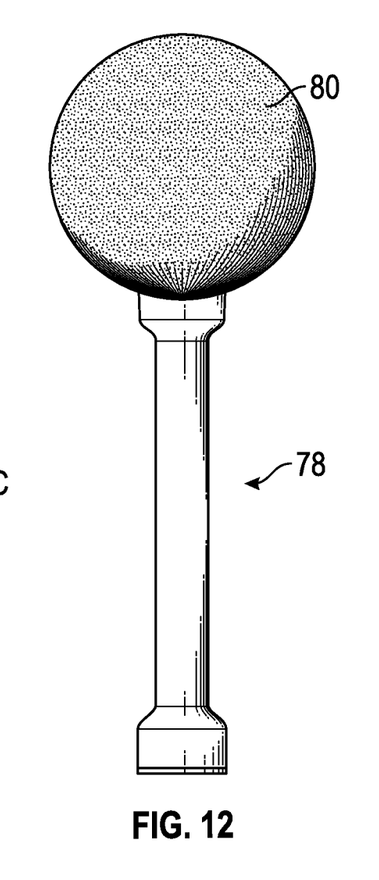
FIG. 12 is a top plan view illustrating another embodiment of the buffing or polishing sponge device having a spherical sponge head.

Any suitable sponge shape or material is contemplated for use with the methods disclosed herein, including the sponge head shape of the first embodiment (FIGS. 1 to 10) as well as the alternative sponge head shapes of FIG. 11A to 12, as well as other shapes. In alternative embodiments, the preparation sponge device may be of more oval, Q-tip like shape, or may comprise a sponge or instrument wipe wrapped around a finger. However, the sponge head shape of FIGS. 1 to 10 is found to work well in reducing the risk of causing injury or epi-defects while improving delivery of ophthalmic solution to the cornea, due to the generally rounded shape as well as the elimination of any sharp edges in the eye preparation surface portion when the sponge is wetted and expands as seen in FIGS. 7 to 9. The sponge heads of FIG. 11A to 11C will also expand to a rounded, partially or completely spherical shape on wetting. The spherical sponge head of FIG. 12 is already completely expanded and rounded prior to use and absorbs liquid at a faster wicking rate than the heads of the other embodiments which are of dry compressed foam. The sponge heads in any of the preceding embodiments may be pre-wetted either prior to application to the eye or by placing on the eye surface to absorb tears, after which the head tends to swell or expand to a more rounded off shape with no sharp edges in the partially spherical tissue preparation surface.

Figure 13:
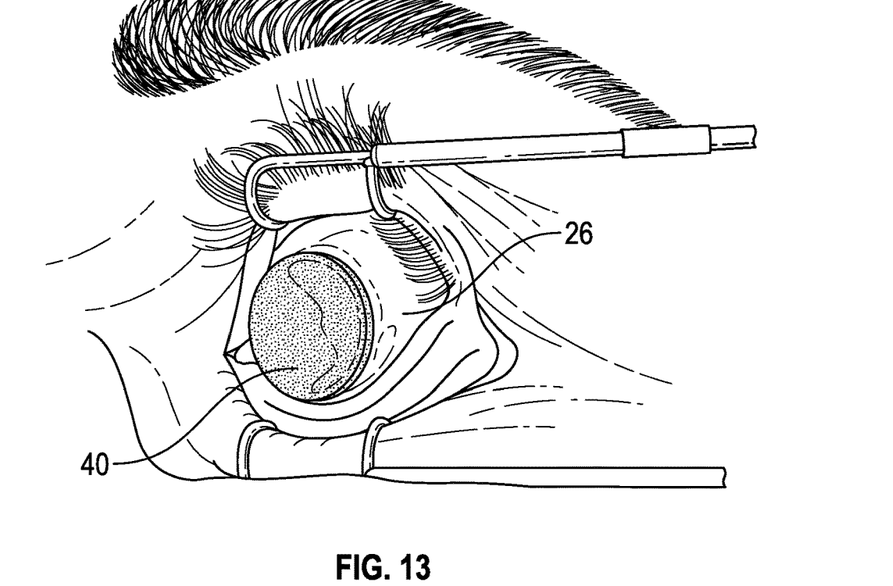
FIG. 13 is a perspective view illustrating an embodiment of a second sponge device or loading sponge placed on an eye for holding and loading of an ophthalmic treatment solution.
Figure 14:
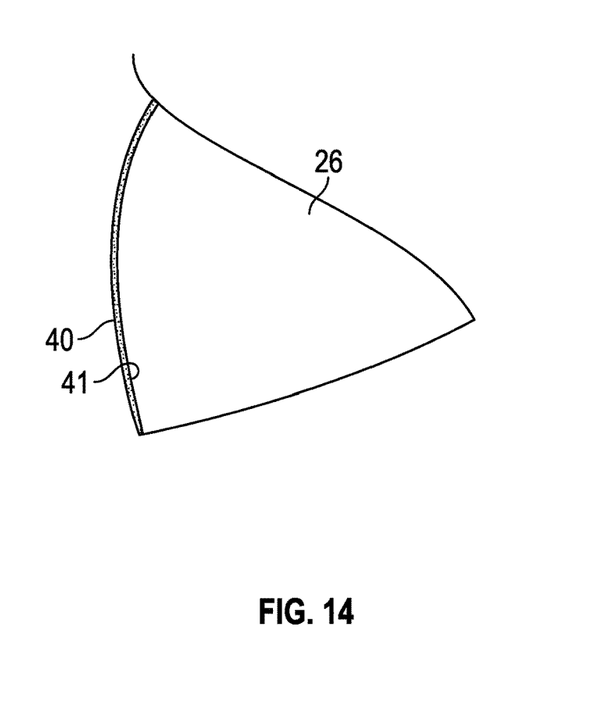
FIG. 14 is a vertical cross-sectional view illustrating the second sponge device of FIG. 13 following the curvature of most of the eye surface, with details of the eye itself omitted.
Figure 15:
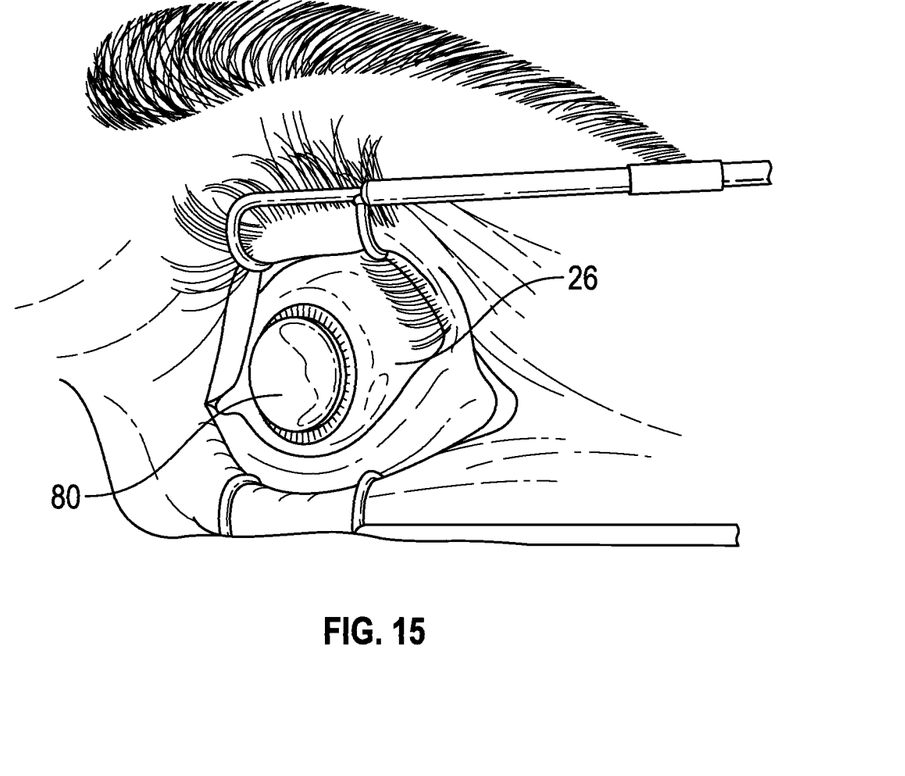
FIG. 15 is a perspective view similar to FIG. 13 illustrating a modified embodiment of a round loading sponge.

After completion of the polishing or buffing step, an ophthalmic solution is applied to the eye in any suitable manner. In some embodiments, the ophthalmic solution is applied through a second sponge device which comprises a solution holding or loading/moistening sponge 24 placed over the eye 26 as illustrated in FIGS. 13 and 14. Sponge 40 of FIG. 13 is circular and is thin enough to form to the curvature of the eye surface 41, as illustrated in FIG. 14. In some embodiments, solution holding or loading sponge 40 is of diameter large enough to cover or drape over all or most of the eye when centrally positioned as illustrated in FIGS. 13 and 14, while in other embodiments, a smaller diameter loading sponge 80 which covers the corneal area of the eye only may be used, as illustrated in FIG. 15, depending on the desired treatment area. In the embodiment of FIGS. 13 and 14, the sponge diameter is in the range from about 10 mm to about 12 mm, and has a thickness of the order of about 0.5 mm to about 3 mm. In one embodiment, the sponge diameter is about 11.5 mm. FIG. 15 illustrates smaller diameter solution holding or loading sponge 80 which covers at least the corneal area of the eye and may have a diameter in the range from about 3 mm to about 9 mm. In some embodiments, the sponges 40 and 80 are in the range of about 0.5 mm to about 5 mm in thickness. In some embodiments, the sponge becomes more flexible when soaked in ophthalmic solution so that it adopts the curvature of the eye when placed and thus contacts most of the area of the eye to allow the solution to penetrate through the epithelium into the cornea or other underlying regions of the eye. Sponge 40 may also be pre-formed in a dry state to conform or fit to the curvature of the eye surface. Although FIGS. 13 and 15 illustrate the eye being held open by a speculum during the solution loading procedure, this is often not necessary either for the eye preparation step of FIG. 12 or the loading procedure using sponge 40 or 80. In fact, the surgeon may hold the eye open manually during these procedures, or in some cases the patient may simply try not to blink.

In some embodiments, the ophthalmic solution is dripped onto the holding or loading sponge while it is placed over the eye, or the sponge is pre-soaked with the ophthalmic solution, or both. The second, loading sponge, for example sponge 40 or 80, acts as a reservoir to hold the solution against the eye surface and to allow application of additional solution. Simply dropping ophthalmic solution directly onto the eye surface or placing drops onto the eye results in the drops running off the eye, and has a limited effect. In contrast, the solution holding sponge of this embodiment places ophthalmic solution directly against the surface of the eye in a location where treatment is needed over an extended time period, allowing more efficient penetration into the cornea. In some embodiments, the ophthalmic solution is a riboflavin solution of 0.2% to 10.0% by weight riboflavin in an aqueous carrier, and optionally, sodium iodide, catalase, artificial tear solution or any combination thereof. If the sponge is pre-loaded with riboflavin, it is stored in a dark packaging material prior to use to avoid or reduce light degradation. In some embodiments, the riboflavin solution contains other additives for increased cross-linking, for example additives as described in PCT Application Publication No. WO 2013/148896. In some embodiments, the sponge is round, but the sponge may be of other shapes (such as oval or eye shaped) in alternative embodiments. In some embodiments, the solution holding or loading sponge operatively covers all or a portion of the eye or the cornea. In some embodiments, the holding sponge is made from any suitable sponge material such as cellulose or any fast wicking, lint-free material such as polyvinyl acetate, for example any of the materials described above in connection with the manipulation or preparation sponge devices of FIGS. 1 to 12. The sponge material of both the preparation sponge device 20 and the holding or loading sponge 40 in one embodiment was PVA sponge material with a pore size in the range of about 60 microns to about 1000 microns. In one embodiment, the pore size of both sponges was in the range from about 60 to about 120 microns. In one example, the pore size was about 60 microns. In one embodiment, the holding or loading sponge may have a larger pore size than the preparation sponge 24 in order to hold more liquid for corneal loading purposes.

Where the sponge is a round sponge, the sponge operatively covers all or a portion of the eye or the cornea. In some embodiments, the size of the sponge does not exceed the size of the eye or the cornea. In some embodiments, the diameter of the sponge is about 3 mm to about 12 mm. In some embodiments, the sponge is about 1 mm to about 5 mm in thickness. A series of different diameter loading sponges may be provided for selection by the physician depending on the desired treatment area.

The above sponges may be used in the two stage method described above for enhanced, faster penetration of any ocular treatment solution through the epithelium and into the cornea, while reducing or minimizing the risk of epithelial defects. The ophthalmic solution may be an ocular riboflavin solution for use in corneal treatment such as photochemical cross linking, or for other ophthalmic uses. In one embodiment, the method may be used for application of a riboflavin solution which contains 0.1 wt. % to 5.0 wt. % riboflavin in an aqueous carrier solution, or up to 10.0% in some cases. In some embodiments, the solution contains about 0.5 wt. % riboflavin. In other examples, the solution contains about 1.0 wt. % riboflavin or about 2.0 wt. % riboflavin. The higher concentration of riboflavin can increase corneal cross-linking if associated with higher amounts of oxygen in the cornea. The riboflavin solution may be stored in an actinic glass or UV and visible light protected plastic containers prior to use, to avoid activation of the riboflavin by ambient light.

The above devices and methods are designed to increase permeability of the epithelium layer with low or minimal epithelial defects resulting from the preparation or tissue manipulation step. Results of testing show that use of the sponge of FIGS. 1 to 9 with a part-circular edge, which expands to a part-spherical or ball-like shape when wetted, may eliminate or substantially eliminate epithelial defects. Similar results may be achieved with the sponges of FIGS. 11A to 11C with a completely circular edges, which also expand to a completely or partially spherical shape, as well as the sponge device of FIG. 12, which is pre-expanded to a spherical shape. Methods using the preparation sponge device of FIGS. 1 to 9 and the loading or holding sponge device of FIGS. 13 to 15 have also been found to significantly reduce the time needed for sufficient riboflavin solution to penetrate into and saturate the cornea, as compared to the time needed with no pre-treatment of the epithelium to increase permeability. Some examples are provided below.

EXAMPLE

Two formulations of riboflavin solution were tested to determine saturation or riboflavin solution loading time after pre-treatment of the epithelium using the preparation sponge devices of the above embodiments. Formulation 1 had a riboflavin concentration of 0.1%. Formulation 2 had a riboflavin concentration of 0.5%. Results are compared in FIG. 16.

Saturation was determined using "serial slit-lamp assessments" of the cornea at approximately 5 minute intervals. Riboflavin has a characteristic green color when illuminated with visible light. Slit-lamp assessments using visible light reveal the depth and uniformity of riboflavin throughout the corneal thickness.

Inclusion Criteria:

Patients who had undergone trans-epithelial cross-linking in one or both eyes were included in the analysis. Patients with a diagnosis of keratoconus or post-LASIK ectasia were included in this analysis.

Exclusion Criteria:

Patients with previous RK, INTACS, more than one cross-linking procedure per eye, and/or patients who were pseudo-phakic or had a diagnosis of nuclear sclerotic cataract were excluded from this analysis.

Results—Formulation 1, 0.1% Riboflavin, Formulation 2, 0.5% Riboflavin

Figure 16:
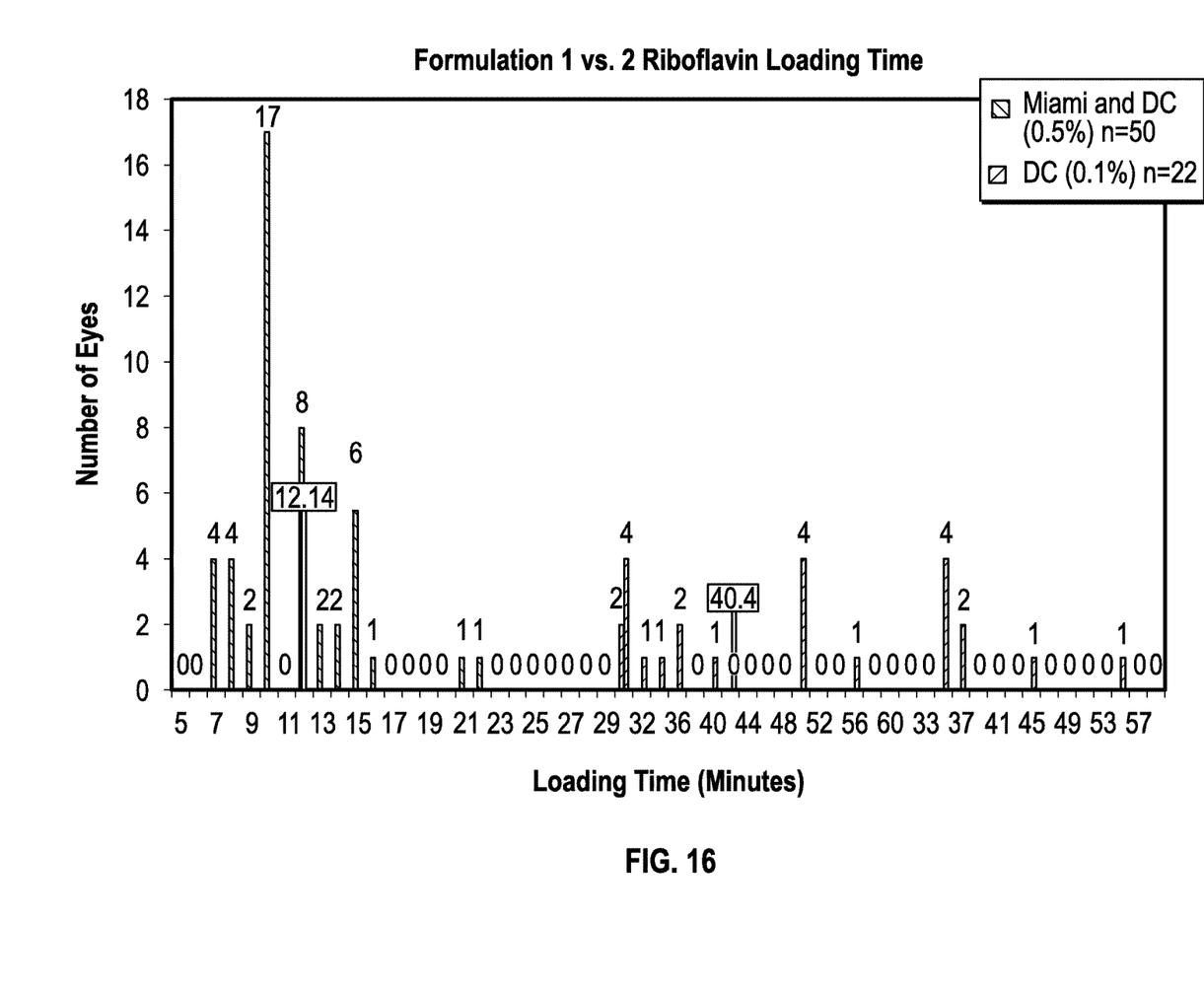
FIG. 16 illustrates tabulated examples of corneal saturation or loading times (in minutes) for a 0.1% riboflavin solution and a 0.5% riboflavin solution when the epithelium is prepared or manipulated with the sponge device of FIGS. 1 to 9 and one of the solution holding or loading sponges of FIGS. 13 to 15 is used to load the riboflavin treatment solution.

The results are shown in FIG. 16. Trans epithelial loading time using one of the loading sponges described above with formulation 1 ranged from 30 minutes minimum to 56 minutes maximum, with an average loading time of 40.4 minutes. Trans epithelial loading time with formulation 2 ranged from 7 to 30 minutes with an average loading time of 12.14 minutes.

The time period for good, homogeneous loading of riboflavin solution into the cornea, i.e. trans epithelial riboflavin loading time, was about 10 to 30 minutes using the delivery augmentation and delivery methods described above. Corresponding loading times without removal or pre-treatment of the epithelium can be up to three hours, significantly adding to the overall time for completion of a corneal treatment procedure.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein present exemplary embodiments of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

We claim:

1. A sponge device for use in preparation of the epithelium of an eye prior to application of an ophthalmic solution, comprising:
    a handle having an end portion; and
    a head secured to the end portion of the handle, the head being formed entirely from a single absorbent, fast wicking sponge material;
    wherein the head is configured to expand from a first configuration having a circular disk shape or part circular disk shape with opposite flat surfaces when dry to a second configuration different from the first configuration and having a spherical or part spherical shape when wetted, at least the second configuration having no sharp edges and comprising an epithelial tissue preparation surface configured for rubbing across the surface of an eye.

2. The device of claim 1, wherein the head has a peripheral rim of at least part circular shape in the first configuration, and the end portion of the handle is exposed in the first configuration and enclosed by the expanded, spherical or part spherical head in the second configuration.

3. The device of claim 2, wherein the peripheral rim of the head has a part-circular portion and a straight rim portion facing away from the part-circular portion in a dry condition, and the end portion of the handle is secured at the center of the straight rim portion and has spaced gripping portions defining a recess in which a central portion of the head is engaged, whereby the end portion grips and restricts the central portion of the head from expanding when the head is wetted.

4. The device of claim 3, wherein the part-circular portion of the rim is at least a semi-circle.

5. The device of claim 4, wherein the part-circular portion is greater than a semi-circle.

6. The device of claim 2, wherein the peripheral rim is of circular shape.

7. The device of claim 2, wherein the thickness of the head in the dry condition is in the range from about 0.5 mm. to about 3 mm.

8. The device of claim 7, wherein the thickness of the head in the dry condition is about 1 mm.

9. The device of claim 2, wherein the diameter of the head is in the range from about 4.5 mm. to about 8 mm.

10. The device of claim 1, wherein the sponge material comprises cellulose or polyvinyl acetate.

11. The device of claim 10, wherein the pore size of the sponge material is in the range from 60 to 120 microns.

12. The device of claim 11, wherein the pore size is about 60 microns.

13. A delivery system for delivery of ophthalmic solutions to the eye, comprising:
a first, eye surface preparation sponge device comprising a handle and a head secured to the handle, wherein the head is formed entirely from a single absorbent, fast-wicking sponge material and is configured to expand from a first configuration having a first shape and dimensions when dry into a second configuration having a second shape and dimensions different from the first configuration when wetted, at least the second configuration being generally rounded with no sharp edges and comprising an epithelial tissue preparation surface of predetermined shape configured for rubbing across the surface of the epithelium of an eye to prepare the surface for penetration by ophthalmic solutions; and
a second, loading sponge device of absorbent, fast-wicking sponge material comprising a disk-shaped sponge having a continuous circular periphery with no indents, opposite flat faces and no opening, a predetermined diameter and a thickness less than the diameter, wherein the disk-shaped sponge has increased flexibility when wetted and loaded with an ophthalmic solution and is configured to cover at least the corneal portion of the eye with no portion of the underlying cornea exposed and to adopt the curvature of the underlying eye surface when wetted with the ophthalmic solution and centrally placed over the eye for loading of ophthalmic solution into the eye after preparation of the eye surface with the first sponge device.

14. The delivery system of claim 13, wherein at least one of the sponges is pre-wetted with an ophthalmic solution.

15. The delivery system of claim 14, wherein the loading sponge device is pre-wetted with an ophthalmic solution.

16. The delivery system of claim 13, wherein the sponge material of the first sponge device and the second sponge device is cellulose or polyvinyl acetate sponge material.

17. The delivery system of claim 13, wherein the thickness of the head of the first sponge device in the first configuration is in the range from about 0.5 mm. to about 3 mm.

18. The delivery system of claim 17, wherein the thickness of the second, disk-shaped sponge device is about the same as the thickness of the head of the first sponge device.

19. The delivery system of claim 13, wherein the circular, disk-shaped sponge has a diameter in the range from about 3 mm to about 12 mm.

20. The delivery system of claim 19, wherein the diameter of the circular, disk-shaped sponge is in the range from about 8 mm to about 12 mm.

21. The delivery system of claim 13, wherein the head of the first sponge device has opposite flat surfaces and a peripheral rim of at least part circular shape, the handle has an end portion secured to a central portion of the head in the first configuration and the head is configured to expand into a substantially ball-like shape enclosing the end portion of the handle in the second configuration.

22. The delivery system of claim 21, wherein the peripheral rim of the head has a part-circular rim portion and a straight rim portion facing away from the part-circular portion in the first configuration, and the end portion of the handle is secured at the center of the straight rim portion and engages the opposite flat surfaces of a central portion of the head in the first configuration, whereby the end portion grips and restricts the central portion of the head from expanding when the head is wetted.

23. The delivery system of claim 22, wherein the part-circular portion of the rim extends around an arc comprising at least a semi-circle.

24. The delivery system of claim 22, wherein the part-circular portion extends around an arc greater than a semi-circle.

25. The delivery system of claim 21, wherein the peripheral rim is of circular shape.

26. The delivery system of claim 13, wherein the head of the first sponge device is of spherical or part spherical shape in the second configuration.

27. The delivery system of claim 13, wherein the sponge material of both sponges has a pore size in the range from about 60 microns to about 1000 microns.

28. The delivery system of claim 27, wherein the pore size of the sponge material of both sponges is in the range from about 60 microns to about 120 microns.

29. The delivery system of claim 28, wherein the pore size is about 60 microns.

* * * * *